United States Patent [19]

Bickford

[11] Patent Number: 5,294,313

[45] Date of Patent: Mar. 15, 1994

[54] SENSORS FOR MONITORING WASTE GLASS QUALITY AND METHOD OF USING THE SAME

[75] Inventor: Dennis F. Bickford, Aiken, S.C.

[73] Assignee: The United States of America as represented by the United States Department of Energy, Washington, D.C.

[21] Appl. No.: 934,394

[22] Filed: Aug. 25, 1992

[51] Int. Cl.$^5$ .................................... G01N 27/26
[52] U.S. Cl. .................... 204/153.15; 204/421; 204/422
[58] Field of Search .............. 204/422, 423, 416, 421, 204/153.15, 153.18

[56] References Cited

U.S. PATENT DOCUMENTS

| | | | |
|---|---|---|---|
| 3,630,874 | 12/1971 | Olette et al. | 204/195 |
| 3,816,269 | 6/1974 | Wilder et al. | 204/1 |
| 4,007,106 | 2/1977 | Hone et al. | 204/195 |
| 4,045,319 | 8/1977 | Deportes et al. | 204/195 |
| 4,313,799 | 2/1982 | Perkins | 204/1 |
| 4,428,770 | 1/1984 | Worrell et al. | 75/45 |
| 4,639,304 | 1/1987 | Bader et al. | 204/413 |

Primary Examiner—T. Tung
Assistant Examiner—Bruce F. Bell
Attorney, Agent, or Firm—Brian R. Tumm; Harold M. Dixon; William R. Moser

[57] ABSTRACT

A set of three electrical probes for monitoring alkali and oxygen activity of a glass melt. On-line, real time measurements of the potential difference among the probes when they are placed in electrical contact with the melt yield the activity information and can be used to adjust the composition of the melt in order to produce higher quality glass. The first two probes each has a reference gas and a reference electrolyte and a pair of wires in electrical connection with each other in the reference gas but having one of the wires extending further into the reference electrolyte. The reference gases both include a known concentration of oxygen. The third electrode has a pair of wires extending through an otherwise solid body to join electrically just past the body but having one of the wires extend past this junction. Measuring the potential difference between wires of the first and second probes provides the alkali activity; measurement of the potential difference between wires of the second and third probes provides the oxygen activity of the melt.

12 Claims, 1 Drawing Sheet

SENSORS FOR MONITORING WASTE GLASS QUALITY AND METHOD OF USING THE SAME

The U.S. Government has rights in the present invention pursuant to Contract No. DE-AC09-89SR18035 between the U.S. Department of Energy and Westinghouse Savannah River Company.

BACKGROUND OF THE INVENTION

1. Field of the Invention

The present invention relates to measurements of physical characteristics of glass melts in order to predict the quality of the glass produced. In particular, the present invention relates to a set of probes that individually and in combination yield information about the oxygen and alkali activity of the glass melt.

2. Discussion of Background

Probes used for measuring, monitoring, or determining the quality or content of molten mixtures, including glass during production, are well known. Typically, such probes are constructed to generate an electrical signal responsive to the oxygen content of a fluid sample. Stabilized zirconium oxide is often used as a reference electrolyte in such devices.

As is well known, when two gases containing oxygen are located on either side of an electrolyte, a potential difference will be established by the movement of oxygen ions between the gases through the electrolyte. The magnitude of the voltage, E, is given by the Nernst equation:

$$E = (RT/4F) \ln (P_1 P_2),$$

where R is the gas constant; T, the absolute temperature; F, the Faraday constant; $P_1$, the partial oxygen pressure of the reference gas; and $P_2$ the partial oxygen pressure of the unknown gas. Thus, the partial pressure of an unknown sample gas present on one side of the electrolyte can be measured if a gas having a known partial pressure is present on the other side of the electrolyte.

Similarly, systems for determining oxygen activity in molten metals, which are based on the same principle, are also known in the art. For instance, Worrell, et al (U.S. Pat. No. 4,428,770) describe a device for determining the sulfur, carbon, and oxygen concentration of molten metal mixtures.

U.S. Pat. Nos. 3,630,874 (Olette, et al.) and 4,007,106 (Hone, et al.) also describe devices for measuring oxygen concentration and activity in molten metal samples by electrochemical means. Olette, et al use a disposable electrochemical cell, which is immersed in the molten sample, to determine the oxygen activity of the sample based on the electric potential across a set of thermocouple terminals.

Perkins, in U.S. Pat. No. 4,313,799, describes a sensor of zirconium oxide for determining oxygen activity in molten glass during the production of textile glass fibers. Also, the exterior portion of the sensor is protected by platinum, thereby extending its life to about one month for noncontinuous use.

Unlike gas probes that are expected to last for long times, probes for molten metals have short term use life expectancies (usually 30 to 60 seconds), as the molten metal environment consumes the probe. Hone et al, in U.S. Pat. No. 4,007,106, details a device used for continuous measurement of oxygen activity and concentration in molten metal samples.

The device in Hone et al provides continuous monitoring without suffering the effects of thermal shock that are usually caused by continuous immersion of a device in molten metal. The device maintains an inert gas atmosphere between the device's reference electrolyte and the molten metal as the device is inserted into the molten metal, thus allowing proper operation without contact between the molten metal and the reference electrolyte.

It is believed that nothing in the foregoing suggests the simultaneous use of more than one probe and measurements taken between the probes to determine molten mixture quality and durability.

SUMMARY OF THE INVENTION

According to its major aspects and broadly stated, the present invention is a system of three electrical probes that are used individually and in combination to determine the alkali and oxygen activities of a glass melt. The three thermocouples produce temperature information by measuring the electrical potential across two wires in each probe, the wires of each probe being made of dissimilar materials and in electrical contact with each other. Moreover, by measuring the electrical potentials among the probes when they are placed in electrical connection with the melt, the alkali and oxygen activities of the melt can be determined.

The first probe comprises a partially hollow shell having a capillary formed in it and communicating with the hollowed portion. A reference gas and a reference electrolyte are placed in the hollowed portion so that the electrolyte can flow into the capillary and into contact with the melt. The two wires are positioned so that they are in electrical contact when in the gas but only one of the wires extends into the electrolyte.

The second probe also comprises a hollow shell with a reference gas and a reference electrolyte, the latter positioned to be in contact with the melt. The two wires of the second probe are in electrical contact in the reference gas but, as in the case of the first probe, the first wire extends into the reference electrolyte.

The third probe comprises a solid body through which two wires extend, joining just beyond the body and having one of the wires extending beyond the wire junction.

The reference gases are both oxygen or a gas mixture in which one of the constituents is oxygen. The reference electrolyte of the first probe is a glass, preferably one that is compatible with the material of the shell. The reference electrolyte of the second probe is preferably zirconium oxide. The shell materials are preferably alumina.

The potential difference between the first and second probes, measured between the wires of each extending into the electrolytes, is related to the alkali activity. The potential difference between the second and third probes measured, in the second probe, at the wire extending into the electrolyte and, at the third probe, at the wire extending into the melt, is related to the oxygen activity.

An important feature of the present invention is the use of three different probes, simultaneously inserted into the melt, to determine electrical potentials related to alkali and oxygen activities which are related to the composition and the oxidation-reduction state of the glass melt and therefore, ultimately, to the quality of the glass. The advantage of this feature is that the composition can be adjusted based on real time, on-line measurements and kept within tolerances, thereby avoiding delay in the manufacture of the glass.

Another feature of the present invention is the capillary in the first probe. The capillary reduces the amount of electrolyte, preferably a glass electrolyte, that is in contact with the glass melt and increases the amount of shell material, $Al_2O_3$. Since the $Al_2O_3$ is more resistant to the effects of the hot glass, the first probe will last longer than otherwise.

Other features and advantages of the present invention will be apparent to those skilled in the art from a careful reading of the Detailed Description of a Preferred Embodiment presented below and accompanied by the drawings.

DETAILED DESCRIPTION OF A PREFERRED EMBODIMENT

Figure 1:
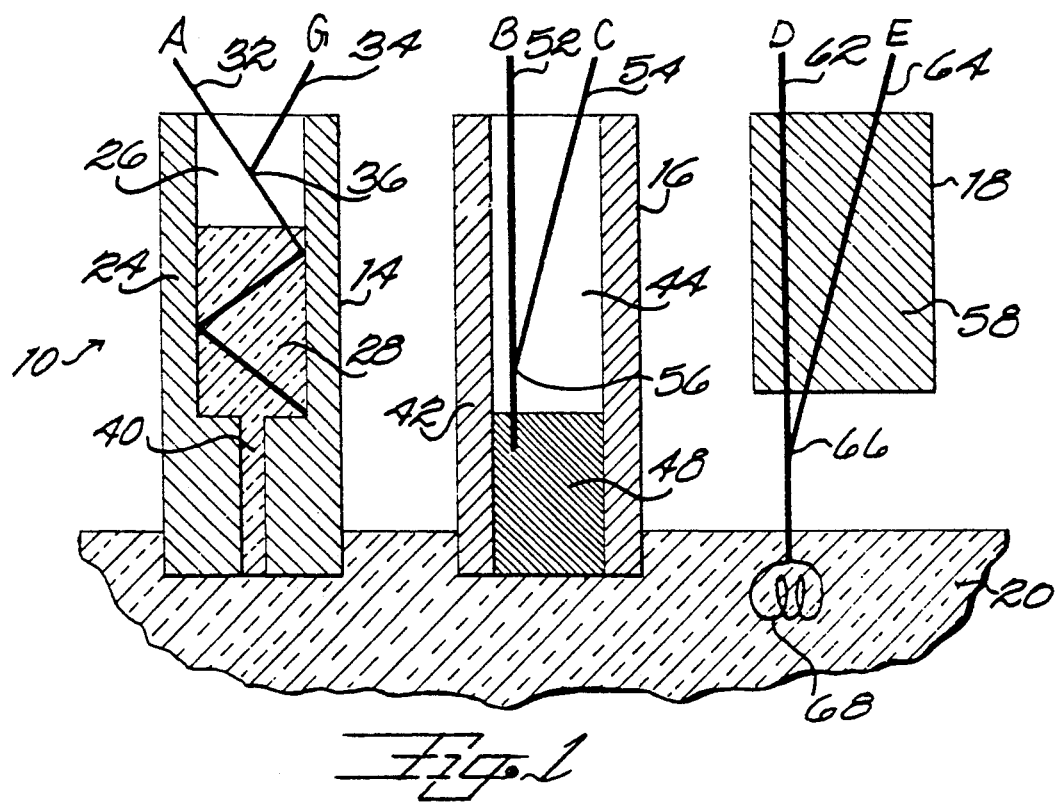
FIG. 1 is a side cross sectional view of the three probes of the probe system according to a preferred embodiment of the present invention.

Referring now to FIG. 1, an electrochemical probe sensing system 10 preferably comprises a set of three probes 14, 16, and 18. Probes 14, 16, and 18 are used to monitor the ion activity of a melt 20, such as molten glass during manufacture of glass or in the incorporation of other materials in a glass matrix. Melt 20 can also be adapted for use with a gaseous or other fluid mixture such as a molten metal. Preferably, probes 14, 16, and 18 are relatively long and thin, each approximately 12-18 inches in length and approximately 0.5 inches in diameter, for example.

The first probe, probe 14 comprises a partially hollow shell 24 made of $Al_2O_3$. Shell 24 contains a reference gas 26 and a reference electrolyte 28. Reference gas 26 can be air or any other gas containing oxygen and having a known partial oxygen pressure.

Reference electrolyte 28 is preferably made of a material compatible with the material of shell 24. Preferably, reference electrolyte 28 is a glass mixture having the approximate composition: 75% $SiO_2$, 7% $Al_2O_3$, 3% $Fe_2O_3$, and a combination of alkali oxides which combination does not exceed 15%. The alkali oxides could be, for example, >5% $Na_2O$, >5% $K_2O$, and >5% $Li_2O$ but is selected to suit the glass being monitored. The high content of $SiO_2$ and $Al_2O_3$ in reference glass 28 provides stability with shell 24 that is also made of $Al_2O_3$.

A pair of probe wires 32, 34 are inserted into probed 14. Preferably, wire 32 (denoted in FIG. 1 as wire A) is made of platinum and wire 34 (denoted in FIG. 1 as wire G) is made of an alloy of platinum and rhodium. Wires 32, 34 are configured within shell 24 with a junction 36 between them so that wires 32, 34 are in electrical connection at junction 36 and a voltage potential exists across them that is proportional to the temperature at junction 36. Thus, wires 32, 34 are used in part as a standard thermocouple to monitor the temperature of reference gas 26 at junction 36, which is preferably located just above the surface of reference electrolyte 28. Wire A extends into reference electrolyte 28.

The lower portion of probe 14 has a capillary 40 for providing electrical and fluid communication between reference glass 28 and melt 20. Preferably, capillary 40 is approximately 1.5 inches long and 0.015 inches or less in diameter. When device 10 is used in proper operation, capillary 40 fills with reference glass 28.

Probe 16 comprises a cylindrical shell 42 preferably made of $Al_2O_3$. Shell 42 contains a reference gas 44 and a reference electrolyte 48. Reference gas 44 can be air or any other gas having a known partial oxygen pressure, similar to reference gas 26 in probe 14. Reference electrolyte 48, located in the lower portion of probe 16, is preferably stabilized or partially stabilized zirconium dioxide.

Also, probe 16 has a pair of wires 52, 54 extending down into the interior of shell 42. Wire 52 (denoted in FIG. 1 as wire B) is made of platinum and wire 54 (denoted in FIG. 1 as wire C) is made of an alloy of platinum and rhodium. The voltage across wires 52, 54 is used to monitor the temperature of reference gas 44 at a junction 56, which is preferably located just above reference electrolyte 48. Wire B extends onto the surface of electrolyte 48. The upper surface of electrolyte 48 may be covered with a porous coating of platinum for better contact.

Probe 18 comprises a body 58 supporting a pair of thermocouple wires 62, 64. Wires 62, 64 extend through body 58 to the lower portion of probe 18. Preferably, wire 62 (denoted in FIG. 1 as wire D) is made of platinum and wire 64 (denoted in FIG. 1 as wire E) is made of an alloy of platinum and rhodium. The voltage across wires 62, 64 is used to monitor the temperature at a junction 66, which is preferably located just above melt 20. Wire D extends beyond the junction of wires D and E. A coil 68, loop or plate of similar material may be connected to the end of wire D and immersed in the glass to minimize the effects of differences between the surfaces and bulk glass being measured.

In addition to using the voltages across wires 32 and 34, 52 and 54, and 62 and 64 to monitor operating temperatures at various locations, wires 32, 52, and 62 are also used in various combinations to monitor other characteristic properties of melt 20. Such combinations and characteristic properties are discussed below.

In use, a powdered mixture of materials that forms reference glass 28 is poured into probe 14. Probes 14, 16, and 18 are then lowered simultaneously into a furnace containing melt 20 until just the tips of probes 14 and 16, and a sufficient area of 18 contact melt 20. The operating temperature of the melt furnace causes the powdered materials in probe 14 to melt, resulting in the formation of reference glass 28. A small portion of reference glass 28 then flows into capillary 40, thereby establishing electrical communication between reference glass 28 and melt 20. The only part of probe 18 in electrical contact with melt 20 is wire D and any similar material attached to wire D to increase its surface area.

Initially, voltage readings across wires 32 and 34, 52 and 54, and 62 and 64 are taken to verify that temperatures at the respective junctions 36, 56, 66, are the same or within the allowed tolerance. Otherwise, error correction factors will have to be introduced later to account for the temperature deviations among the probes. Thereafter, wires 34, 54, and 64 are used as thermocouples only to verify operating temperatures throughout the monitoring process.

Then, the voltage potential between wire 32 of probe 14 and wire 52 of probe 16 is used for monitoring continuously the alkali activity of melt 20 as compared to the alkali activity of reference glass 28. Alkali activity is a composition-dependent characteristic of a fluid such as melt 20. Furthermore, the alkali activities of melt 20 and reference glass 28 are related through the Nernst equation.

Since alkali activity is generally inversely proportional to the viscosity, and consequently the durability, of melt 20, the composition of melt 20 can be modified as needed to adjust its measured alkali activity. Thus, continuously monitoring the alkali activity of melt 20 through instantaneous voltage measurements enables the production of glass having the desired durability or viscosity.

Additionally, the oxygen activity of melt 20 as compared to the oxygen activity of reference electrolyte 48 can be monitored through voltage measurements across wires 52 and 62. This measurement can be used in conjunction with the Nernst equation to determine the oxygen content of a sample fluid such as melt 20. Therefore, it provides an additional parameter for determining the composition of melt 20.

The previously discussed melt characteristics are represented in device 10 as voltage measurements across certain materials. That is, alkali activity measurements of melt 20 (across wires 32 and 52) are represented by the voltage potential across reference glass 28, melt 20, and reference electrolyte 48. Similarly, oxygen activity measurements of melt 20 (across wires 52 and 62) are represented by the voltage potential across electrolyte 48, as measured between wires 52 and 62.

In measuring the alkali activity of melt 20, the effect of the voltage potential across reference electrolyte 48, in addition to potentials across reference glass 28 and melt 20, nullifies any oxygen activity from the alkali activity relationship. In other words, measurements taken across reference glass 28 and melt 20 only (say, from wire 32 of probe 14 to wire 62 of probe 18) would represent the alkali activity and oxygen activity of melt 20 as compared to the alkali activity and oxygen activity of reference glass 28. Therefore, the use of probes 14 and 16 allows the two activities to be separated and measured individually.

The continuous measurement from wire 32 to wire 62 can still be used for monitoring melt 20. Such measurements would be made, for instance, when probe 16 was unavailable due to physical or cost constraints. Also, melt measurements using just probes 14 and 18 can be made when a lower degree of measurement accuracy will suffice in a particular application. Similarly, wires 34, 54 or 64 may be eliminated in specific applications where the detailed measurements of temperatures of the respective probes are not required.

The novel configuration of probe 14 can be made inexpensively by a well known slip casting technique. Slip casting, for the most part, involves molding and baking a particular workpiece. Thus probe 14 can be slip cast or formed as one piece, with the interior shaped as shown in FIG. 1, including the formation of capillary 40. Prior sensing probes, such as probe 16, are slip cast as two pieces (shell 42 and reference electrolyte 48) that have to be cemented together, thus taking longer and costing more than a one-piece slip casting manufacturing technique.

Device 10, when used to continuously monitor the quality of the composition of melt 20 during its manufacture, can help to reduce the overall batch preparation time. By providing continuous monitoring rather than periodic sampling, device 10 allows melt 20 to be removed from the furnace as soon as the desired durability qualities are met. Conversely, current monitoring methods require batches of melt 20 to remain in the furnace longer than necessary, delaying completion of manufacture.

It will be apparent to those skilled in the art that many changes and substitutions can be made to the preferred embodiment herein described without departing from the spirit and scope of the present invention as defined by the appended claims.

What is claimed is:

1. A probe system for determining oxygen and alkali activity of a glass melt, said system comprising:
   a first probe having
      a first conducting wire,
      a second conducting wire,
      a first quantity of oxygen, and
      a first reference electrolyte adjacent said first quantity of oxygen,
      said first wire in electrical connection with said first wire,
      said first and second wires placed in said second quantity of oxygen and said first wire extending onto said first reference electrolyte;
   a second probe having
      a first wire,
      a second wire,
      a second quantity of oxygen, and
      a second reference electrolyte adjacent to said second quantity of oxygen,
      said first wire in electrical communication with said second wire,
      said first and second wires placed in said second quantity of oxygen and said first wire extending into said second reference electrolyte; and
   a third probe having
      a first wire,
      a second wire in electrical connection with said second wire,
      said first wire extending beyond said second wire,
   said first, second and third probes positioned in spaced relation in said melt, said first and said second reference electrolytes and said first wire of said third probe being in electrical connection with said melt so that a first electrical potential difference can be measured across said first wire of said first probe and said first wire of said second probe, and a second electrical potential difference can be measured across said first wire of said second probe and said first wire of said third probe,
   said first measurement indicating alkali activity of said melt and said second measurement indicating oxygen activity of said melt.

2. The probe system as recited in claim 1, wherein said first probe further comprises a shell having formed therein a hollow and a capillary tube, said capillary tube communicating between said hollow and said melt, said first reference gas and said first reference electrolyte contained within said hollow, said reference electrolyte flowing through said capillary to said melt when heated.

3. The probe system as recited in claim 1, wherein said first probe further comprises a shell made of $Al_2O_3$ and having formed therein a hollow and a capillary tube, said capillary tube communicating between said hollow and said melt, said first reference gas and said first reference electrolyte contained within said hollow, said reference electrolyte flowing through said capillary to said melt when heated.

4. The probe system as recited in claim 1, wherein said first probe further comprises a shell having formed therein a hollow, said first reference gas and said first reference electrolyte contained within said hollow, said shell made of a material, said first reference electrolyte composed in part of said material selected to be compatible with said shell.

5. The probe system as recited in claim 1, wherein said first probe further comprises a shell having formed therein a hollow and a capillary tube, said capillary tube communicating between said hollow and said melt, said first reference gas and said first reference electrolyte contained within said hollow, said first reference electrolyte flowing through said capillary to said melt when heated, said first reference electrolyte made of a mixture including approximately 75% $SiO_2$, approximately 7% $Al_2O_3$, approximately 3% $Fe_2O_3$ and a combination of alkali oxides, said combination not exceeding approximately 15%.

6. The probe system as recited in claim 1, wherein said first probe further comprises a shell made of $Al_2O_3$ and having formed therein a hollow and a capillary tube, said capillary tube communicating between said hollow and said melt, said first reference gas and said first reference electrolyte contained within said hollow, said first reference electrolyte flowing through said capillary to said melt when heated, said first reference electrolyte made of a mixture including approximately 75% $SiO_2$, approximately 7% $Al_2O_3$, approximately 3% $Fe_2O_3$, and a combination of alkali oxides, said combination not exceeding 15%.

7. The probe system as recited in claim 1, wherein said second reference electrolyte of said second probe is made of zirconium dioxide.

8. A probe system for determining oxygen and alkali activity of a glass melt, said system comprising:
a first probe having
a shell with a hollow and a capillary formed therein, said capillary communicating with said hollow,
a first conducting wire,
a second conducting wire,
a first quantity of oxygen in said hollow, and
a first reference electrolyte in said hollow and adjacent to said first quantity of oxygen,
said first wire in electrical connection with said second wire and placed in said quantity of oxygen,
said first wire extending into said first reference electrolyte;
a second probe having
a shell having a hollow,
a first wire,
a second wire,
a second quantity of oxygen in said hollow, and
a second reference electrolyte in said hollow and adjacent to said second quantity of oxygen,
said first wire in electrical connection with said second wire and placed in said second quantity of oxygen,
said first wire extending into said second reference electrolyte; and
a third probe having
a body,
a first wire carried by and extending through said body,
a second wire carried by and extending through said body and in electrical connection with said second wire outside said body,
said first wire extending beyond said second wire,
said first, second and third probes positioned in spaced relation in said melt, said first and said second reference electrolytes and said first wire of said third probe being in electrical connection with said melt, said first reference electrolyte flowing through said capillary to said melt when heated, so that a first electrical potential difference can be measured across said first wire of said first probe and said first wire of said second probe, and a second electrical potential difference can be measured across said first wire of said second probe and said first wire of said third probe,
said first measurement indicating alkali activity of said melt and said second measurement indicating oxygen activity of said melt.

9. The probe system as recited in claim 8, wherein said shell of said first probe and said shell of said second probe are made of $Al_2O_3$.

10. The probe system as recited in claim 8, wherein said shell of said first probe is made of $Al_2O_3$ and said first reference electrolyte is a glass composed of approximately 7% $Al_2O_3$.

11. The probe system as recited in claim 8, wherein said first wires of said first, second and third probe are made of platinum and said second wires of said first, second and third probes are made of a platinum and rhodium alloy.

12. A method for determining the alkali and oxygen activities of a glass melt, said method comprising the steps of:
placing a first reference electrolyte in electrical connection with said melt;
placing a second reference electrolyte in electrical connection with said melt and spaced apart from said first reference electrolyte;
placing a conducting wire in electrical communication with said melt and in spaced relation to said first and second reference electrolytes;
measuring a first potential difference between said first reference electrolyte and said second electrolyte; and
measuring a second potential difference between said second reference electrolyte and said conducting wire
said first potential difference being proportional to said alkali activity and said second potential difference being proportional to said oxygen activity.

* * * * *